US006591832B1

(12) United States Patent
DeJonge

(10) Patent No.: US 6,591,832 B1
(45) Date of Patent: Jul. 15, 2003

(54) DRY POWDER DISPENSER

(75) Inventor: Stuart DeJonge, Easton, PA (US)

(73) Assignee: Saint-Gobain Calmar Inc., City of Industry, CA (US)

( * ) Notice: Subject to any disclaimer, the term of this patent is extended or adjusted under 35 U.S.C. 154(b) by 0 days.

(21) Appl. No.: 10/078,487

(22) Filed: Feb. 21, 2002

(51) Int. Cl.[7] .............................................. A61M 15/00
(52) U.S. Cl. .......................... 128/203.14; 128/203.15; 128/203.21
(58) Field of Search ................. 128/203.12, 203.15, 128/203.21, 203.19, 203.23, 200.11, 200.12, 200.21, 200.23, 200.24, 203.14; 604/58; 206/538, 532

(56) References Cited

U.S. PATENT DOCUMENTS

| 5,161,524 A | * | 11/1992 | Evans ................... 128/203.15 |
| 5,201,308 A | * | 4/1993 | Newhouse ............. 128/203.15 |
| 5,320,714 A | * | 6/1994 | Brendel ................. 128/203.15 |
| 5,349,947 A | | 9/1994 | Newhouse et al. |
| 5,388,572 A | * | 2/1995 | Mulhauser et al. ..... 128/203.15 |
| 5,447,151 A | * | 9/1995 | Bruna et al. ........... 128/203.15 |
| 5,460,173 A | * | 10/1995 | Mulhauser et al. ..... 128/203.15 |
| 5,542,411 A | * | 8/1996 | Rex ....................... 128/203.15 |
| 5,584,417 A | | 12/1996 | Graf et al. |
| 5,881,719 A | * | 3/1999 | Gottenauer et al. ..... 128/203.15 |
| 6,006,747 A | | 12/1999 | Eisele et al. |
| 6,029,662 A | * | 2/2000 | Marcon ................. 128/203.15 |
| 6,123,070 A | * | 9/2000 | Bruna et al. ........... 128/203.15 |
| 6,179,164 B1 | | 1/2001 | Fuchs |
| 6,257,233 B1 | * | 7/2001 | Burr et al. ............. 128/203.15 |
| 6,332,461 B1 | * | 12/2001 | Hyppola ................ 128/203.15 |
| 6,484,715 B1 | * | 11/2002 | Ritsche et al. ......... 128/200.21 |

* cited by examiner

*Primary Examiner*—Weilun Lo
*Assistant Examiner*—Teena Mitchell
(74) *Attorney, Agent, or Firm*—Dykema Gossett PLLC

(57) ABSTRACT

A dry powder dispenser has a base member which supports a blister pack of rupturable pillows each containing measured quantities of dry powder to be dispensed. A pillow aligning with the discharge opening and the base member which likewise has a discharge passage in communication therewith for the discharge of the dry powder as the pillow is ruptured by a hinged lever which displaces the entire contents of the dry powder from its pillow chamber into the discharge passage, the lever sequentially activating an air piston for flow feeding a quantity of pressurized air along the discharge passage to expel the dry powder under air pressure.

11 Claims, 2 Drawing Sheets

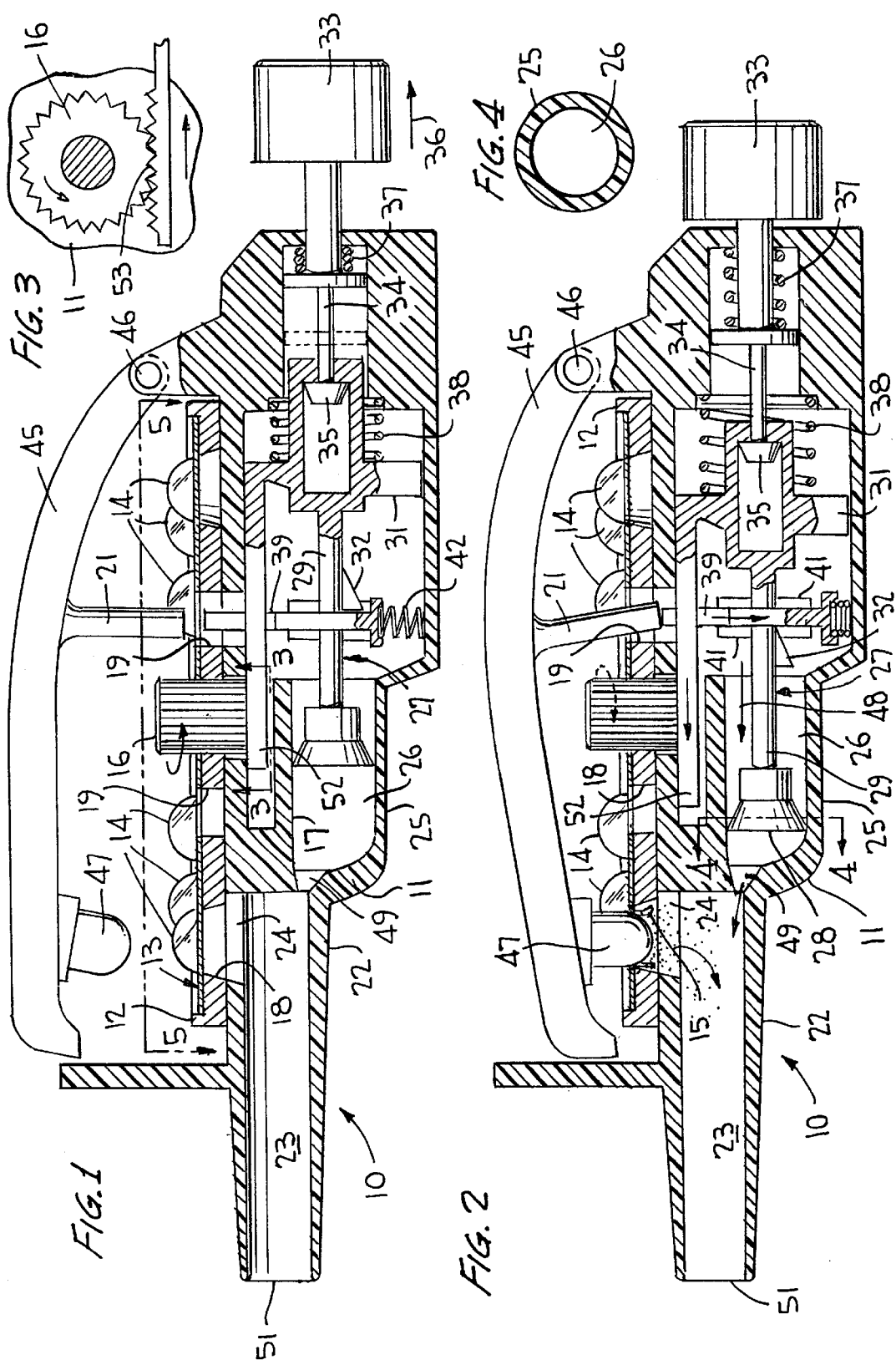

DRY POWDER DISPENSER

BACKGROUND OF THE INVENTION

This invention relates to a hand-held dry powder dispenser, and more particularly to such a dispenser which can accommodate a blister pack of several rupturable pillows containing dry powder to be dispensed for personal care use.

Dry powder dispensers are available for use in expelling especially pharmaceutical media to the respiratory tract, such as through the nose and throat. Some powder dispensers are adapted for a blister pack containing a plurality of metered power packets to be dispensed from rupturable pillows or compartments. A moveable spike or anvil is provided for rupturing the pillow upon manual movement of one section of the dispenser relative to another, whereupon the powder media is free to be expelled through a discharge path of the dispenser.

A known dispenser of the type characterized above is disclosed in U.S. Pat. No. 6,179,164 to Karl-Heinz Fuchs. There the powder dispenser comprises moveable and stationary parts relatively moveable along a central axis. This stationary part supports a blister pack containing powder filled blisters or pillows in a circular array, and the moveable part has a spike and a coaxial discharge nozzle such that upon rotary shifting movement of one of the pillows in alignment with the spike end, inward shifting movement of the manual part ruptures the pillow and exposes the powder to the discharge nozzle. The moveable and stationary parts together include air piston and cylinder units, such that upon relative movement of the parts together air under pressure is forced through a one-way valve in the stationary part for directing the pressurized air to the exposed powder causing it to be expelled out through the nozzle discharge.

The prior art powder dispenser as aforedescribed is not without its drawbacks. For example, the air piston stroke is limited by the maximum spacing between the stationary and moveable parts, and the path of movement of the compressed air before it reaches the exposed powder is quite circuitous. For example, the path of the air is first axial, then outwardly radial and then again axial requiring an abrupt 90° turn. Because of the short stroke and the circuitous nature of the air path, air under sufficient pressure is unavailable at each stroke for adequately and completely expelling the loose powder from the discharge nozzle. Besides, since only a foil backing of the pillow is ruptured for freeing the powder contents of the pillow, the likelihood of completely expelling the powder from its opened pillow by the movement of a circuitous and short stroke air path, is limited.

There is need to improve upon the known dry powder dispensers to ensure that the entirety of the measured media is expelled from the ruptured capsule in a manner which is efficient, effective, and economical.

SUMMARY OF THE INVENTION

It is therefore an object of the present invention to provide a dry powder dispenser of the type which accommodates a blister pack supporting measured quantities of a plurality of powder media, the blisters being ruptured one-at-a-time by a moving anvil with the freed powder media being forced out through the discharge by a burst of air under pressure.

To this end the dry powder dispenser according to the invention assures expelling of the entire contents of each of the capsules of the blister pack on incremental rupture thereof. The dispenser is structured such that the blister is completely emptied of its powder contents upon rupture by the anvil as the contents drop under gravity into a discharge passage at which time a puff of compressed air discharges the powder from the dispenser.

The dry powder dispenser of the invention includes a base supporting at least one medium reservoir having an hermetically sealed and openable dry powder containing chamber which aligns with the discharge opening in the base. A discharge passage in the base communicates with the discharge opening, and means are provided in the base for flow feeding a quantity of pressurized air along the discharge passage. A hinged lever on the base displaces the dry powder from its chamber, upon actuation thereof which sequentially activates the air feeding means.

Another objects, advantages, and novel features of the invention will become more apparent from the following detailed description of the invention when taken in conjunction with the accompanying drawings.

BRIEF DESCRIPTION OF THE DRAWINGS

FIG. 1 is a side elevational view, shown largely in section, of the powder dispenser according to the invention at a position with the air piston charged for firing;

FIG. 2 is a view similar to FIG. 1 showing the dispenser when activated for discharge of the powder;

FIG. 3 is a plan view taken substantially along the line 3—3 of FIG. 1 of means for rotating the blister pack;

FIG. 4 is sectional view taken substantially along the line 4—4 of FIG. 2;

DETAILED DESCRIPTION OF THE INVENTION

Figure 5:
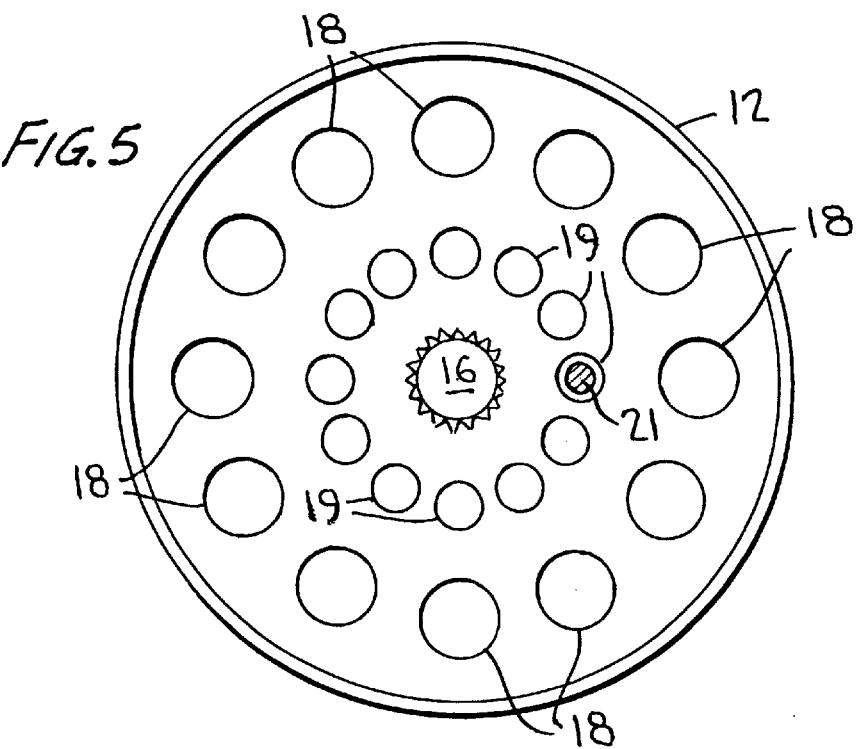
FIG. 5 is a view taken substantially along the line 5—5 of FIG. 1.

Turning now to the drawings wherein like reference characters refer to like and corresponding parts throughout the several views, the dispenser according to the invention is generally designated 10 in FIGS. 1 and 2 and includes a base member 11 which may be of a suitable molded plastic material of a relatively small size readily adaptable to be cradled in a hand of the operator. The base member supports a turntable 12 which may be of circular configuration on which rests an assembly 13 of a plurality of rupturable capsules or pillows 14 each containing a measured quantity of powder media of some specific type usable for especially nasal and throat applications. Typically the chamber formed by the pillow containing the powder is closed by a tearable foil 15 or the like (see FIG. 2), such that assembly 13 may be in the form of the well-known blister pack. As more clearly shown in FIG. 5, turntable 12 engages a splined post 16 mounted for free rotation on a forked arm 17 of the base member. The turntable has a plurality of openings 18 arranged in a circular array (FIG. 5) at which each of the pillows 14 is located. The turntable further has openings 19 likewise arranged in a circular array through which a firing pin 21 extends in a manner and for the purpose as described in detailed hereinafter.

The base member of the dispenser has an elongated discharge barrel 22 defining a discharge passage 23 through which a metered amount of product is discharged under the assistance of a puff of air according to the invention. At the root or inner end of the discharge barrel is a discharge opening 24 in open communication with passage 23 and in axial alignment with one of the openings 18 of the turntable.

The base member has a cylindrical shaped portion 25 (FIG. 4) defining a pump cylinder having a pump bore 26. within which an air piston 27 operates. The air piston has a piston cup 28 in sliding sealing engagement with cylindrical bore 26, and a piston stem 29 having a caged terminal end 31.

The air piston is designed to be cocked in readiness to be "fired" by firing pin 21 during operation of the dispenser. The piston stem has a piston catch 32 which may be in the form of a depending triangular element shown in FIGS. 1, 2, 6 and 7. Piston 27 is retracted to its firing position of FIG. 1 by manually pulling knob 33 in a direction shown by arrow 36 away from the base member, the knob having a stem 34 terminating in a boss 35 engaging an inner wall of cage 31. When the knob is pulled in the direction of arrow 36 against the bias of its spring 37, boss 35 causes the air piston to be shifted into its firing position of FIG. 1 against the bias of its spring 38.

Figure 6:
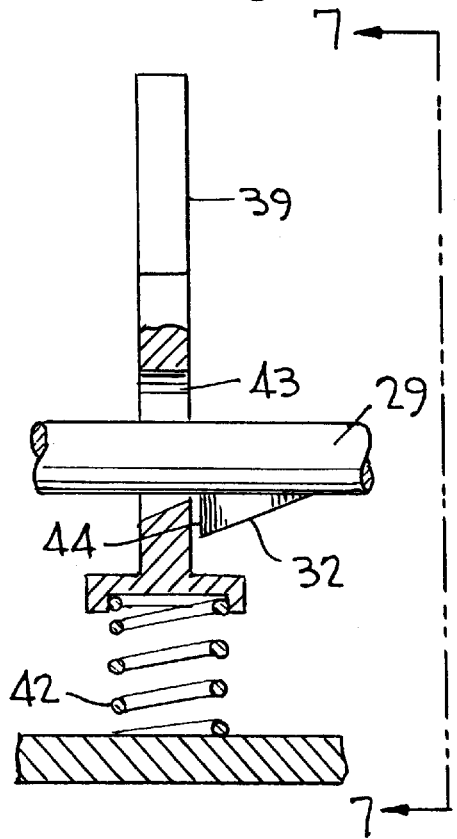
FIG. 6 is an enlarged side view, partially in section, of the cocked piston stem.
Figure 7:
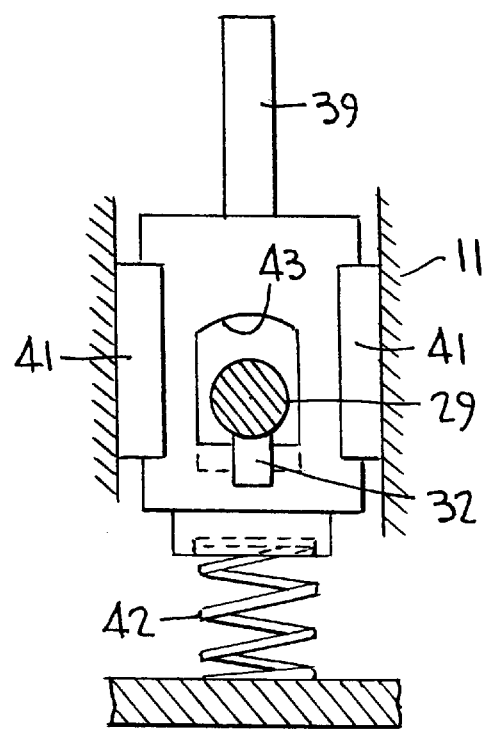
FIG. 7 is a side elevational view taken substantially along the line 7—7 of FIG. 6.

A firing yoke 39 is mounted within the base member for sliding movement between pairs of guide plates 41, and is supported in its position of FIGS. 6, 7 by a compression spring 42. The firing yoke has an oversized opening 43 through which piston stem 29 extends such that when the knob is pulled outwardly causing the piston to shift in the direction of arrow 36, the piston catch 32 slides through opening 43 and in the process depresses yoke 39 against its spring 42 permitting the catch to clear opening 43 so as to come to rest in its FIGS. 1 and 6 position where radial face 44 of the catch bears against a confronting face of yoke 39. When the operator releases knob 33 it shifts to its position shown in phantom outline in FIG. 1 under the assistance of its spring 37.

A dispensing actuator is provided in the form of a lever arm 45 hinged to the base member as at 46, the firing pin 21 depending from the arm and in alignment with firing yoke 39. The lever arm also has a depending anvil 47 which may have a blunt end as shown or which may have a pointed end, the anvil being in alignment with discharge opening 24. Thus, when the dispenser is placed in the firing position of FIG. 1, movement by the operator of lever arm 45 toward the base member about hinge 46 functions to rupture one of the pillows or capsules 14 in alignment with opening 24 which, as shown in FIG. 2, causes the entirety of the contents of the ruptured pillow to fall by gravity and displacement into discharge passage 23. Sequentially with the rupturing of the blister, firing pin 21 engages yoke 39 causing it to shift downwardly against its spring 42, permitting catch 32 to clear opening 43 and permitting the air piston to shift forwardly in the direction of arrow 48. Thus air that was entrained in bore 26 is forced under pressure by the piston through reduced opening 49 causing the air to enter passage 23 under pressure for simultaneously producing an air burst causing the powder in the discharge passage to be expelled therefrom through terminal discharge orifice 51.

This base member further has an indexing arm 52 having ratchet teeth 53 on its inner edge (FIG. 3) which engages splined post 16 while the piston is shifted from its FIG. 2 back to its FIG. 1 firing position. This engagement causes rotation of post 16 in the direction of the curved arrow shown for correspondingly rotating turntable 12 and with it the blister pack 13. The degree of rotation of post 16 is set so as to index a single pillow 14 into and out of alignment with discharge opening 24. Thus, each time the knob 33 is pulled outwardly to charge the piston, the blister pack is rotated for indexing the next powder filled pillow into alignment with anvil 47. When the lever arm is lowered and the firing pin 21 trips the yoke to permit the piston to shift forwardly, arm 52 is made to disengage from post 16 in any normal manner known in this art, and to re-engage with the splines of the post prior to the arm being again shifted back into its FIG. 1 position. Such technology is known and forms no part of the invention.

The dry powder dispenser according to the invention as aforedescribed is of simple construction which is easy to fabricate, yet is highly efficient in expelling the entire contents of the rupturable pouch of a blister pack into, for example, the respiratory duct of the user. Few parts are required to fabricate the dispenser which is easy to use with little instructions. For example, the operator simply lifts lever 45 pivoting it about its hinge 46 and places a circular blister pack 13 onto the top surface of turntable 12, post 16 extending through a central opening in the pack. The dry powder filled pillows 14 are respectively aligned with their openings 18 in the turntable by the provision of some type of orienting means acting between assembly 13 and turntable 12, such as, for example, a key and a keyway. Also it should be pointed out that a hinged lid (not shown) may be provided as hinged to base member 11 covering the circular blister pack, the hinge being clasped in place in some manner to base member 11. A nasal adaptor hood (not shown) which may be provided to cover the discharge barrel 22 for sanitary purposes, would then be removed, and the operator thereafter pulls outwardly on knob 33 which charges the air piston and places it in the "firing" position of FIG. 1. The operator then expels the contents of one of the pillows 14 into his nose or throat or whatever, by simply depressing lever 45 to the FIG. 2 position. When the lever is lowered about its hinge 46 to the FIG. 2 position, handle 47 ruptures pillow 14 thereby emptying the powder contents into discharge passage 23 as the entirety of the contents fall by gravity and displacement into this passage. Sequentially therewith, firing pin 21 depresses yoke 39 shifting it downwardly against the force of its spring 42 and permitting catch 32 to pass forwardly in the direction of arrow 48 through opening 43 which thereby releases the piston causing the piston head to force air from air chamber 26 under pressure through constricted opening 49 into discharge passage 23. This forced air provides a burst of air to the fallen dry powder and expels it completely and neatly out of the discharge end 51 of the nozzle. For subsequent usage, the operator again pulls knob 33 outwardly in the direction of arrow 36 which again places the air piston into its firing position of FIG. 1 and which simultaneously indexes the next pillow 14 into alignment with opening 24 as indexing arm 52 rotates splined post 16 in the direction of the curved arrow as shown. This subsequent dispensing is carried out as aforedescribed.

Obviously, many modifications and variations of the present invention are made possible in the light of the above teachings. It is therefore to be understood that within the scope of the appended claims the invention may be practiced otherwise than as specifically described.

What is claimed is:

1. A dry powder dispenser, comprising:
 a base member supporting at least one medium reservoir having an hermetically sealed, openable chamber containing a dry powder in alignment with a discharge opening in the base member;
 the base member having a medium discharge passage in communication with the discharge opening for discharging the dry powder;

means within said base member for flow feeding a quantity of pressurized air along said discharge passage; and a lever hinged at one end to said base member and having an anvil for rupturing the reservoir for displacing the dry powder from the chamber into the discharge passage and for simultaneously activating said air feeding means.

2. The dispenser according to claim 1, wherein said base member has a rotatable support for a flat carrier containing a plurality of reservoirs respectively having hermetically sealed, openable chambers each containing a quantity dry powder, means on said base member operable for sequentially locating each said reservoir from an initial position to a readiness position in alignment with said discharge opening.

3. The dispenser according to claim 2, wherein said support is rotatable about a central axis, said locating means comprising an indexing arm engaging a splined shaft on said base at said axis which engages the rotatable support.

4. The dispenser according to claim 2, wherein said flat carrier and said reservoirs comprise a blister pack.

5. The dispenser according to claim 2, wherein the support engages a central splined shaft on the base and is rotatable together therewith, said locating means comprising an indexing arm engaging the shaft during a setting operation of the flow feeding means.

6. The dispenser according to claim 1, wherein said flow feeding means comprises a pump piston and cylinder, the piston being movable to a stored position.

7. The dispenser according to claim 1, wherein the flow feeding means includes a piston and a releasable trip for maintaining the piston in a stored position, and a firing pin for sequentially releasing the trip upon movement of the lever toward a rotatable support for the flat carrier.

8. The dispenser according to claim 1, wherein said flow feeding means comprises an air piston operating in an air cylinder, means for manually setting the piston to a firing position, said lever means having a firing pin engaging said setting means.

9. The dispenser according to claim 8, wherein said setting means includes a spring biased firing yoke, and a catch on the piston engaging a catch on the yoke in the firing position.

10. The dispenser according to claim 9, wherein the piston is spring biased for movement toward the discharge passage upon engagement of the firing pin with the flow feeding means.

11. The dispenser according to claim 1, wherein the hinged lever has a firing pin for activating the air feeding means.

* * * * *